(12) United States Patent
Dietlin et al.

(10) Patent No.: US 10,515,099 B2
(45) Date of Patent: Dec. 24, 2019

(54) MEDICAL CLINICAL TRIAL SITE IDENTIFICATION

(71) Applicant: INTERNATIONAL BUSINESS MACHINES CORPORATION, Armonk, NY (US)

(72) Inventors: Timothy L. Dietlin, Park Ridge, IL (US); Abhinav N. Jain, Cambridge, MA (US); Radhesh B. Nair, Fairfax, VA (US); Ravishankar Rao, Elmsford, NY (US)

(73) Assignee: International Business Machines Corporation, Armonk, NY (US)

(*) Notice: Subject to any disclaimer, the term of this patent is extended or adjusted under 35 U.S.C. 154(b) by 870 days.

(21) Appl. No.: 14/680,469

(22) Filed: Apr. 7, 2015

(65) Prior Publication Data

US 2016/0300040 A1    Oct. 13, 2016

(51) Int. Cl.
*G16H 10/20* (2018.01)
*G06F 16/29* (2019.01)

(52) U.S. Cl.
CPC .............. *G06F 16/29* (2019.01); *G16H 10/20* (2018.01)

(58) Field of Classification Search
CPC .............................. G06Q 50/22; G06Q 50/24
See application file for complete search history.

(56) References Cited

U.S. PATENT DOCUMENTS

| | | | |
|---|---|---|---|
| 6,904,434 B1 | 6/2005 | Wallach et al. | |
| 8,620,680 B2 | 12/2013 | Schultz | |
| 8,706,537 B1 | 4/2014 | Young et al. | |
| 2002/0002474 A1* | 1/2002 | Michelson | G06F 19/322 705/3 |
| 2002/0145617 A1* | 10/2002 | Kennard | G06Q 30/06 345/634 |
| 2004/0010418 A1* | 1/2004 | Buonocore | G06F 19/325 705/2 |

(Continued)

OTHER PUBLICATIONS

Clinical trials GPS launches new patient dashboard suggests trials based on condition and location, connects research facilities with patients in the U.S. (Oct. 31, 2013). PRWeb Newswire Retrieved from http://dialog.proquest.com/professional/docview/1447503640?accountid=142257 (Year: 2013).*

*Primary Examiner* — Lena Najarian
(74) *Attorney, Agent, or Firm* — Schmeiser, Olsen & Watts; Mark C. Vallone

(57) ABSTRACT

A method and system for identifying clinical trial sites is provided. The method includes receiving clinical trial data associated with a plurality of planned clinical trials. Portions of the clinical trial data are identified based on differing data sources. Relevant information is extracted from the portions. Socioeconomic data, demographics data, and epidemiological data are received and combined into a common format. Incorrect address data is corrected and the clinical trial data, socioeconomic data, demographics data, and epidemiological data are standardized. In response, an initial list is generated. The initial list includes associated principle investigators and clinical trial sites associated with planned clinical trials overlaid on the clinical trial data, the socioeconomic data, the demographics data, and the epidemiological data.

21 Claims, 11 Drawing Sheets

(56) References Cited

U.S. PATENT DOCUMENTS

| | | | |
|---|---|---|---|
| 2004/0078216 A1* | 4/2004 | Toto | G06F 19/322 705/2 |
| 2010/0088245 A1* | 4/2010 | Harrison | G06Q 10/10 705/317 |
| 2011/0153361 A1* | 6/2011 | Hanina | G06Q 10/10 705/3 |
| 2012/0290317 A1* | 11/2012 | Nair | G06Q 10/10 705/2 |
| 2013/0151277 A1* | 6/2013 | Thiers | G06F 19/327 705/2 |
| 2013/0304484 A1 | 11/2013 | Martinez et al. | |
| 2013/0304504 A1* | 11/2013 | Powell | G06Q 50/22 705/3 |
| 2014/0222444 A1 | 8/2014 | Cerello et al. | |
| 2014/0236668 A1 | 8/2014 | Young et al. | |
| 2014/0249845 A1 | 9/2014 | Kahn et al. | |

* cited by examiner

Site Locations (US) where Competitors are Present but B is not

Table- City_Competitor Present B Absent Locations

| City | County (US) | State/Province | In / Out of B | Sponsor C | Sponsor A |
|---|---|---|---|---|---|
| Miami | MIAMI-DADE | Florida | Out | 5 | 5 |
| Morristown | MORRIS | New Jersey | Out | | 1 |
| Morton | TAZEWELL | Illinois | Out | | 1 |
| New Port Richey | PASCO | Florida | Out | | 1 |
| New SmyRa Beach | VOLUSIA | Florida | Out | | 1 |
| New Windsor | ORANGE | New York | Out | 2 | |
| Newport | PERRY | Pennsylvania | Out | | 1 |
| North Miami Beach | MIAMI-DADE | Florida | Out | | 1 |
| Ocala | MARION | Florida | Out | 1 | |
| Oveide | SEMINOLE | Florida | Out | | 1 |
| Palm Harbor | PINELLAS | Florida | Out | | 1 |
| Pembroke Pines | BROWARD | Florida | Out | | 1 |

Table- Zip_Competitor Present B Absent Locations

| Zip Code | City | State/Province | In / Out of B | Sponsor C | Sponsor A |
|---|---|---|---|---|---|
| | Bridgewater | New Jersey | Out | | 1 |
| | Daytona Beach | Florida | Out | | 1 |
| | DeLand | Florida | Out | | |
| | Hialeah | Florida | Out | | 1 |
| | Jacksonville | Florida | Out | | 1 |
| | Miami | Florida | Out | | 1 |
| | New Windsor | New York | Out | | 1 |

Sponsor
☐ (All)
☐ Null
☑ A
☐ B
☑ C

In / Out of B
☐ (All)
☐ In
☑ Out

Note: Uncheck "In" and Check "Out" to exclude locations where B is present

Avg. Hyperlipidemia% (All Ages)
50 — 67

Avg. Heart Failure% (All Ages)
12 — 48

Avg. HeartDisease MortalityRate Per...
122 — 440

Year of Trial Completion Date
☑ Null
☑ 2010
☑ 2011
☑ 2012
☑ 2013
☑ 2014
☐ 2015

FIG. 8

MEDICAL CLINICAL TRIAL SITE IDENTIFICATION

FIELD

The present invention relates generally to a method for identifying clinical trial sites and in particular to a method and associated system for using specified data and a correction process to streamline the clinical trial sites based on geographical need.

BACKGROUND

Conducting clinical trials typically includes a lengthy and costly process for pharmaceutical companies. A clinical trial comprises a necessary step before drug approval is granted by regulatory authorities. As a size and complexity of clinical trials continues to increase to possibly tens of thousands of enrolled patients, it is imperative for pharmaceutical companies to be able to identify available patient pools before and during a clinical trial process.

Pharmaceutical companies do not have the tools to quickly identify locations associated with large patient pools. Therefore, the pharmaceutical companies benchmark their clinical trial progress against that of competitors. Accessing a tool a tool to quickly identify locations where large patient pools exist would enable pharmaceutical companies to accelerate their clinical trials, thereby reducing costs and gaining a competitive advantage.

Accordingly, there exists a need in the art to overcome at least some of the deficiencies and limitations described herein above.

SUMMARY

A first aspect of the invention provides a location condition forecasting method comprising: receiving in r A clinical trial site identification method comprising: receiving, by a computer processor of a computing system, clinical trial data associated with a plurality of planned clinical trials, associated locations, and investigators; identifying, by the computer processor, portions of the clinical trial data received from differing data sources; analyzing, by the computer processor, the portions; extracting, by the computer processor based on results of the analyzing, relevant information from the portions; receiving, by the computer processor, socioeconomic data, demographics data, and epidemiological data; combining into a common format, by the computer processor, different sets of data of the clinical trial data, the socioeconomic data, the demographics data, and the epidemiological data; correcting, by the computer processor executing a geo-spatial visualization tool, incorrect address data associated with the associated locations; standardizing, by the computer processor, the clinical trial data, the socioeconomic data, the demographics data, and the epidemiological data; and generating, by the computer processor based on results of the standardizing, an initial list comprising associated principle investigators and clinical trial sites associated with the plurality of planned clinical trials overlaid on the clinical trial data, the socioeconomic data, the demographics data, and the epidemiological data.

A second aspect of the invention provides a computing system comprising a computer processor coupled to a computer-readable memory unit, the memory unit comprising instructions that when executed by the computer processor implements a clinical trial site identification method comprising: receiving, by the computer processor, clinical trial data associated with a plurality of planned clinical trials, associated locations, and investigators; identifying, by the computer processor, portions of the clinical trial data received from differing data sources; analyzing, by the computer processor, the portions; extracting, by the computer processor based on results of the analyzing, relevant information from the portions; receiving, by the computer processor, socioeconomic data, demographics data, and epidemiological data; combining into a common format, by the computer processor, different sets of data of the clinical trial data, the socioeconomic data, the demographics data, and the epidemiological data; correcting, by the computer processor executing a geo-spatial visualization tool, incorrect address data associated with the associated locations; standardizing, by the computer processor, the clinical trial data, the socioeconomic data, the demographics data, and the epidemiological data; and generating, by the computer processor based on results of the standardizing, an initial list comprising associated principle investigators and clinical trial sites associated with the plurality of planned clinical trials overlaid on the clinical trial data, the socioeconomic data, the demographics data, and the epidemiological data.

A third aspect of the invention provides a computer program product, comprising a computer readable hardware storage device storing a computer readable program code, the computer readable program code comprising an algorithm that when executed by a computer processor of a computing system implements a clinical trial site identification method comprising: receiving, by the computer processor, clinical trial data associated with a plurality of planned clinical trials, associated locations, and investigators; identifying, by the computer processor, portions of the clinical trial data received from differing data sources; analyzing, by the computer processor, the portions; extracting, by the computer processor based on results of the analyzing, relevant information from the portions; receiving, by the computer processor, socioeconomic data, demographics data, and epidemiological data; combining into a common format, by the computer processor, different sets of data of the clinical trial data, the socioeconomic data, the demographics data, and the epidemiological data; correcting, by the computer processor executing a geo-spatial visualization tool, incorrect address data associated with the associated locations; standardizing, by the computer processor, the clinical trial data, the socioeconomic data, the demographics data, and the epidemiological data; and generating, by the computer processor based on results of the standardizing, an initial list comprising associated principle investigators and clinical trial sites associated with the plurality of planned clinical trials overlaid on the clinical trial data, the socioeconomic data, the demographics data, and the epidemiological data.

A fourth aspect of the invention provides a process for supporting computing infrastructure, the process comprising providing at least one support service for at least one of creating, integrating, hosting, maintaining, and deploying computer-readable code in a computer system comprising a computer processor, wherein the computer processor, in response to the providing, carries out instructions contained in the code causing the computer system to perform a clinical trial site identification comprising: receiving, by the computer processor, clinical trial data associated with a plurality of planned clinical trials, associated locations, and investigators; identifying, by the computer processor, portions of the clinical trial data received from differing data sources; analyzing, by the computer processor, the portions; extracting, by the computer processor based on results of the analyzing, relevant information from the portions; receiving, by the computer processor, socioeconomic data, demographics data, and epidemiological data; combining into a common format, by the computer processor, different sets of data of the clinical trial data, the socioeconomic data, the demographics data, and the epidemiological data; correcting, by the computer processor executing a geo-spatial visualization tool, incorrect address data associated with the associated locations; standardizing, by the computer processor, the clinical trial data, the socioeconomic data, the demographics data, and the epidemiological data; and generating, by the computer processor based on results of the standardizing, an initial list comprising associated principle investigators and clinical trial sites associated with the plurality of planned clinical trials overlaid on the clinical trial data, the socioeconomic data, the demographics data, and the epidemiological data.

A fifth aspect of the invention provides a clinical trial site identification method comprising: receiving, by a computer processor of a computing system, clinical trial data associated with a plurality of planned clinical trials, associated locations, and investigators; identifying, by the computer processor, portions of the clinical trial data received from differing data sources; analyzing, by the computer processor, the portions; extracting, by the computer processor based on results of the analyzing, relevant information from the portions; receiving, by the computer processor, socioeconomic data, demographics data, and epidemiological data; executing, by the computer processor, a Web scraping process with respect to publically available data of the portions; combining into a common format, by the computer processor based on results of the executing, different sets of data of the clinical trial data, the socioeconomic data, the demographics data, and the epidemiological data; correcting, by the computer processor executing a geo-spatial visualization tool, incorrect address data associated with the associated locations; standardizing, by the computer processor, the clinical trial data, the socioeconomic data, the demographics data, and the epidemiological data; and generating, by the computer processor based on results of the standardizing, an initial list comprising associated principle investigators and clinical trial sites associated with the plurality of planned clinical trials overlaid on the clinical trial data, the socioeconomic data, the demographics data, and the epidemiological data.

The present invention advantageously provides a simple method and associated system capable of quickly identifying locations where large patient pools exist to enable pharmaceutical companies to accelerate their clinical trials determining location conditions.

BRIEF DESCRIPTION OF THE DRAWINGS

FIG. 8 illustrates a table for providing formation and filters to drill down to identify most promising clinical trial sites and PIs, in accordance with embodiments of the present invention.

DETAILED DESCRIPTION

Figure 1:
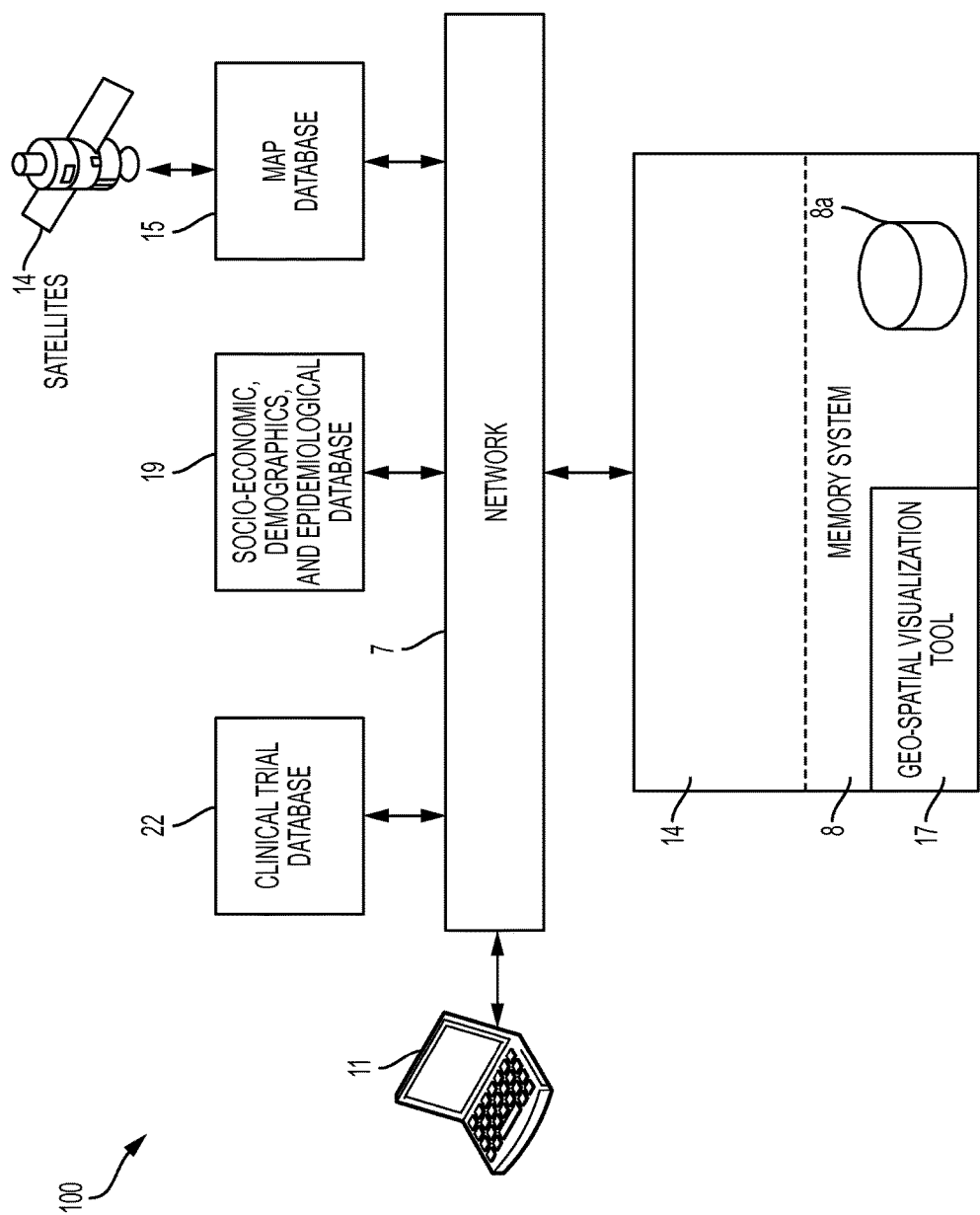
FIG. 1 illustrates a system for identifying and streamlining clinical trial sites based on geographical need, in accordance with embodiments of the present invention.

FIG. 1 illustrates a system 100 for identifying and streamlining clinical trial sites based on geographical need, in accordance with embodiments of the present invention. Various clinical trial identification methods are associated with clinical trials that are already underway. The aforementioned processes do not identify advantageous locations for conducting the clinical trials. Additionally, the aforementioned processes do not project a future location for conducting the clinical trials. Consequently, pharmaceutical companies may be unable to identify locations that include large patient pools. Additionally, typical clinical trial locations do not streamline to specific patient pools. Therefore, system 100 provides a method that solves this problem by accurately identifying clinical trial sites based on geographical need.

System 100 enables a data-driven approach for identifying (medical) clinical trial sites. System 100 analyzes clinical trial data, socioeconomic data, demographics data, epidemiological data, and geographical maps related data for identifying the clinical trial sites. The epidemiological data is analyzed to identify locations for potential patient pools comprising specific disease codes. The clinical trial data comprises publicly available data associated with industry-wide trials for a given disease code or drug class. Additionally, the clinical trial data comprises optional data related to locations for existing trials being conducted by a private party. The analyzed data is triangulated to identify locations satisfying the following constraint: (Location includes significant patient pool) AND (Few competitor trials are already taking place at the location) AND (a private party is not conducting trials at the location). The location may be specified by zip code or by specific medical institutions. An advantage associated with the aforementioned approach comprises providing a global data-driven view of the clinical trial landscape overlaid with respect to demographic data thereby identifying clinical trial sites for consideration as potential clinical trial sites.

System 100 of FIG. 1 includes a clinical trial database 22, a socio-economic, demographics, and epidemiological database 19, a map database 15, and a computing device 11 connected through a network 7 to a computing system 14. Network 7 may include any type of network including, inter alia, a local area network, (LAN), a wide area network (WAN), the Internet, a wireless network, etc. Computing device 11 may include any type of computing device or software/hardware system including, inter alia, a computer (PC), a laptop computer, a tablet computer, a server, a PDA, a smart phone, a secure Website, an application, etc. Map database is communicatively connected to a satellite system 14. Satellite system 14 may comprise any type of satellite system including, inter alia, a global positioning satellite (GPS) based system. Computing system 14 may include any type of computing system(s) including, inter alia, a computer (PC), a laptop computer, a tablet computer, a server, etc. Computing system 14 includes a memory system 8. Memory system 8 may include a single memory system. Alternatively, memory system 8 may include a plurality of memory systems. Memory system 8 includes a database 8a and a geo-spatial visualization tool (software) 17. Geo-spatial visualization tool (software) 17 enables a process for identifying sites for performing clinical trials.

Figure 2A:
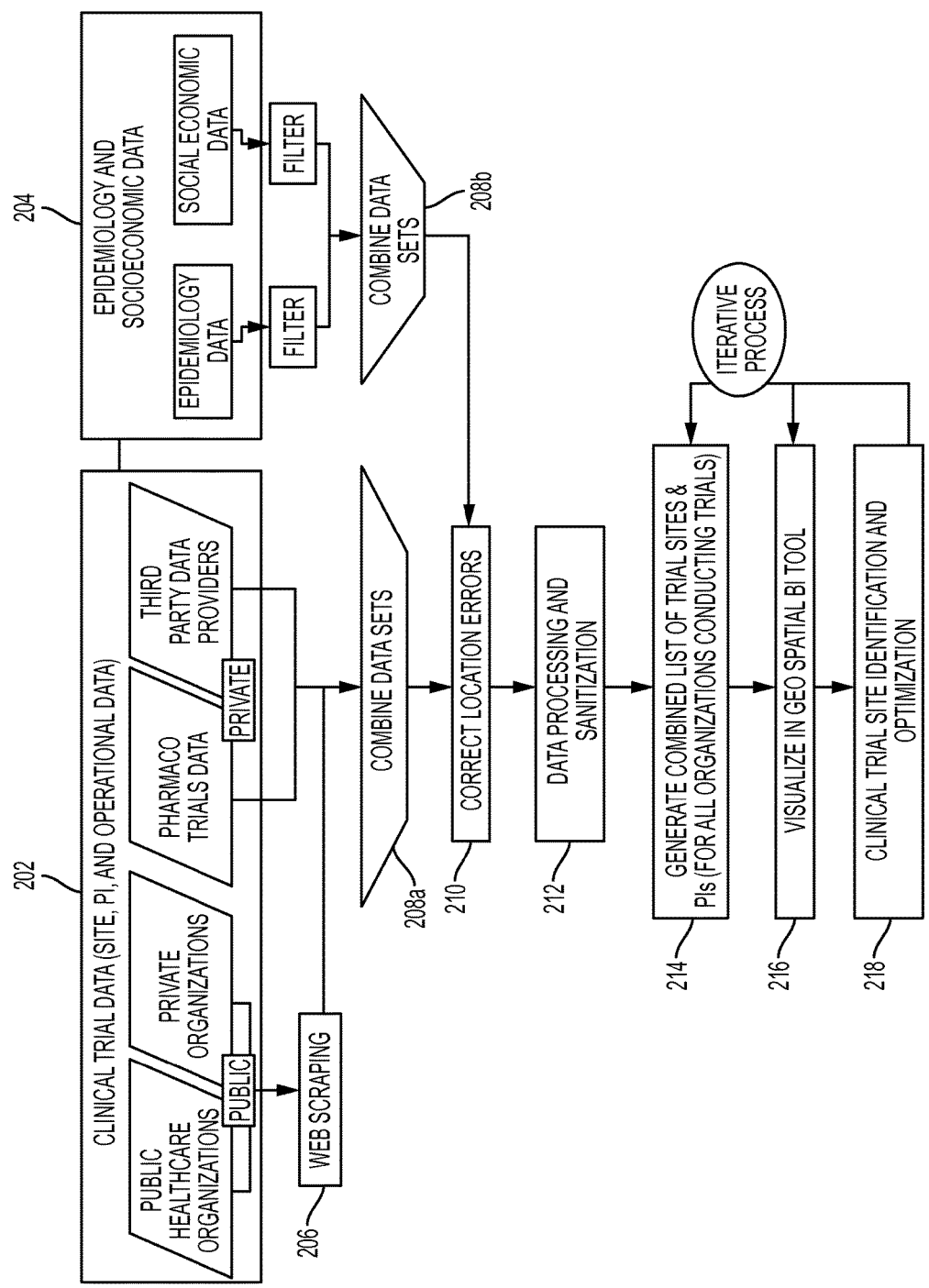
FIGS. 2A-2C, in combination, illustrates an algorithm detailing a process flow enabled by the system of FIG. 1 for identifying and streamlining clinical trial sites based on geographical need, in accordance with embodiments of the present invention.

FIG. 2A illustrates an algorithm detailing a process flow enabled by system 100 of FIG. 1 for identifying and streamlining clinical trial sites based on geographical need, in accordance with embodiments of the present invention. Each of the steps in the algorithm of FIG. 2 may be enabled and executed in any order by a computer processor executing computer code. In step 202, clinical trial data (e.g., site, principal investigator (PI) and operational data) is identified, analyzed, and sourced. The clinical trial data includes global external public/private data sources on the web (freely available public data), internal data sources, and external third party/syndicated data sources from data providers. The global external public/private data sources on the web may include government/public health websites and private organization and company websites. The internal data sources may include pharmaceutical healthcare company related internal operational and research data with respect to existing clinical trial and principal investigators comprising a domain associated with a trial study. The external third party/syndicated data sources from data providers may include data retrieved from third party companies specializing in clinical trials.

In step 204, epidemiology and socioeconomic data is identified, analyzed, and sourced. The epidemiology data may include data retrieved from public health websites and organizations such as the CDC, WHO, and private healthcare and pharmaceutical companies. The socioeconomic data may be retrieved from public organizations such as census studies and private companies such as FICO.

In step 206, a Web scraping process is executed with respect to the identified, analyzed, and sourced clinical trial data of step 202. A Web scraping process is defined herein as a process for extracting (or harvesting) relevant and rich information from the public web, using combination of tools, methods, and algorithms. The Web scraping process may include cataloging extracted data into a structured format at a specified grain of information.

In step 208 (i.e., steps 208a and 208b), all data sets are combined. The differing data sets within the clinical trial data and epidemiology data categories (from various sources including web, public and private companies and organizations, and third party data providers) are combined into a common format for further data processing. In step 210, location errors are corrected. For example, since all retrieved data is gathered from various sources including the web, the data may include erroneous locations/address names. Any locations that do not process within geo spatial visualization tool 17 may require correction. Geo location codes may be used to identify each location within visualization and analytical tools. In step 212, a data processing and sanitization process is executed. The data processing and sanitization process allows system 100 to perform cleansing, sanitization, and standardization of the retrieved data. The data processing and sanitization process may include a process for removing duplicates, using standard location and site naming methods, etc. to improve a quality of data for performing further analysis. In step 214, a combined list of trial sites & PIs (for all Organizations conducting trials) is generated. Step 214 allows for consolidation of all data sources for generation of a structured list of clinical trial sites (of a clinical trial within the scope of study) and principle investigators.

In step 216, a process for visualizing data in the geo-spatial visualization tool 17 (i.e., of FIG. 1) is initiated. The process includes preparing the data, retrieving maps, and filtering selections. In step 218, clinical trial sites are identified.

Figure 2B:
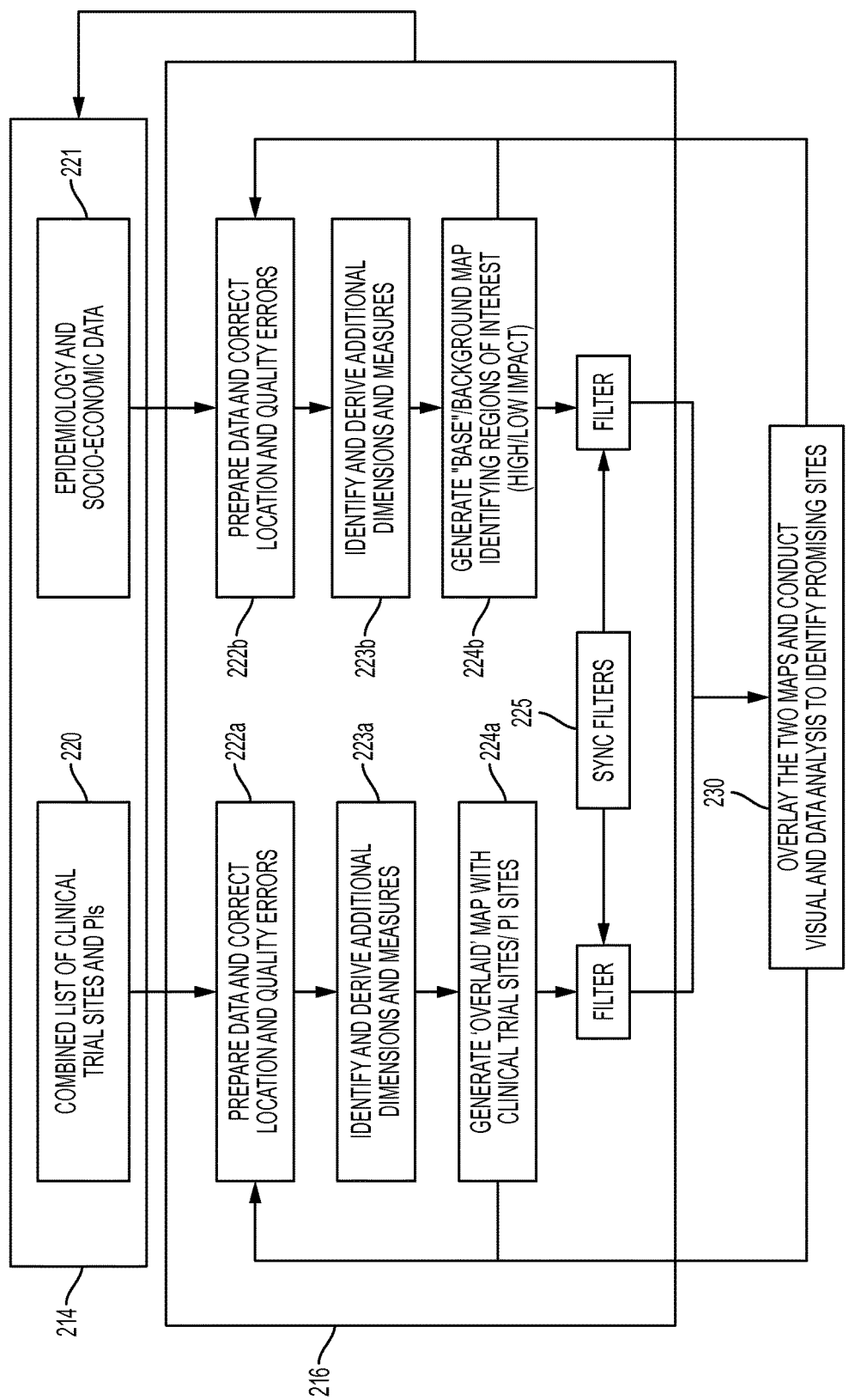

FIG. 2B illustrates a detailed description of steps 214 and 216 of the algorithm of FIG. 2A, in accordance with embodiments of the present invention. In step 220, a combined list of trial sites & PIs (for all Organizations conducting trials) is generated. In step 221, filters are applied and relevant epidemiology and social economic information is identified with respect to the analysis of locating best clinical trial sites and PIs. In steps 222a and 222b data is prepared for the clinical trial sites and the epidemiology and socio-economic data. Preparing the data includes (i.e., after the data from various sources has been combined) preparation for use to use with BI/visualization tools to perform data analysis and generate visualization reports. Raw data from step 214 is used to further derive specific measures to augment data analysis. In steps 223a and 223b, correct dimensions and facts (in the clinical trial sites, epidemiolog, and clinical trial data) are identified and the data is prepared to perform an analysis. The BI tool is additionally used to identify and correct location errors. Additionally, BI tool capabilities may enable identifying duplicates and further sanitize data. A focus of the analysis comprises identifying best targets (location or PI/Institutions) for clinical trials. In steps 224a and 224b, differing maps are leveraged (e.g., a base map, an overlaid map, etc.) at different granularities thereby and providing different (but complimentary) information. The differing maps are overlaid with respect to each other (in step 230) to derive a list of sweet spots/target areas associated with increasing or optimizing clinical trial operational and performance results. A base/background map comprises a map for identifying regions of interest. The regions of interest may differ based on performed analysis. For example, an entity may want to focus on US counties associated with a high prevalence of a disease with respect to an average of all US counties. A base map enables identification of the regions of interest at different granularity levels such as from country and state level down to zip code level. An overlaid map comprises a map associated with pin pointing clinical trial information such as, inter alia, 1. Clinical trial site location address data (on going, completed, future proposed, etc.) associated with being run by different competing organizations.
2. PI site address information from all competing organizations for all clinical trials that are being run in a same therapeutic class of drug that is being trialed. The overlaid map may enable returning current or potential target clinical trial sites or PIs that may be beneficial for clinical trial results.

Filtering selections allow the BI tools to enable using filters within the tool (i.e., to include/exclude certain sets of data) such that a more focused analysis may be performed.

Filters may be applied to raw data or to one or all of the maps that are being used. Filters may be applied to focus on: particular locations of interest, class of disease, class of drugs, competing organizations or trials, PIs, institutions etc. Enabling an advanced setting in the BI tools enables atomization and synchronization of filters across various maps and visuals that in return help to increase analytic performance, repeatability, and quality.

Figure 2C:
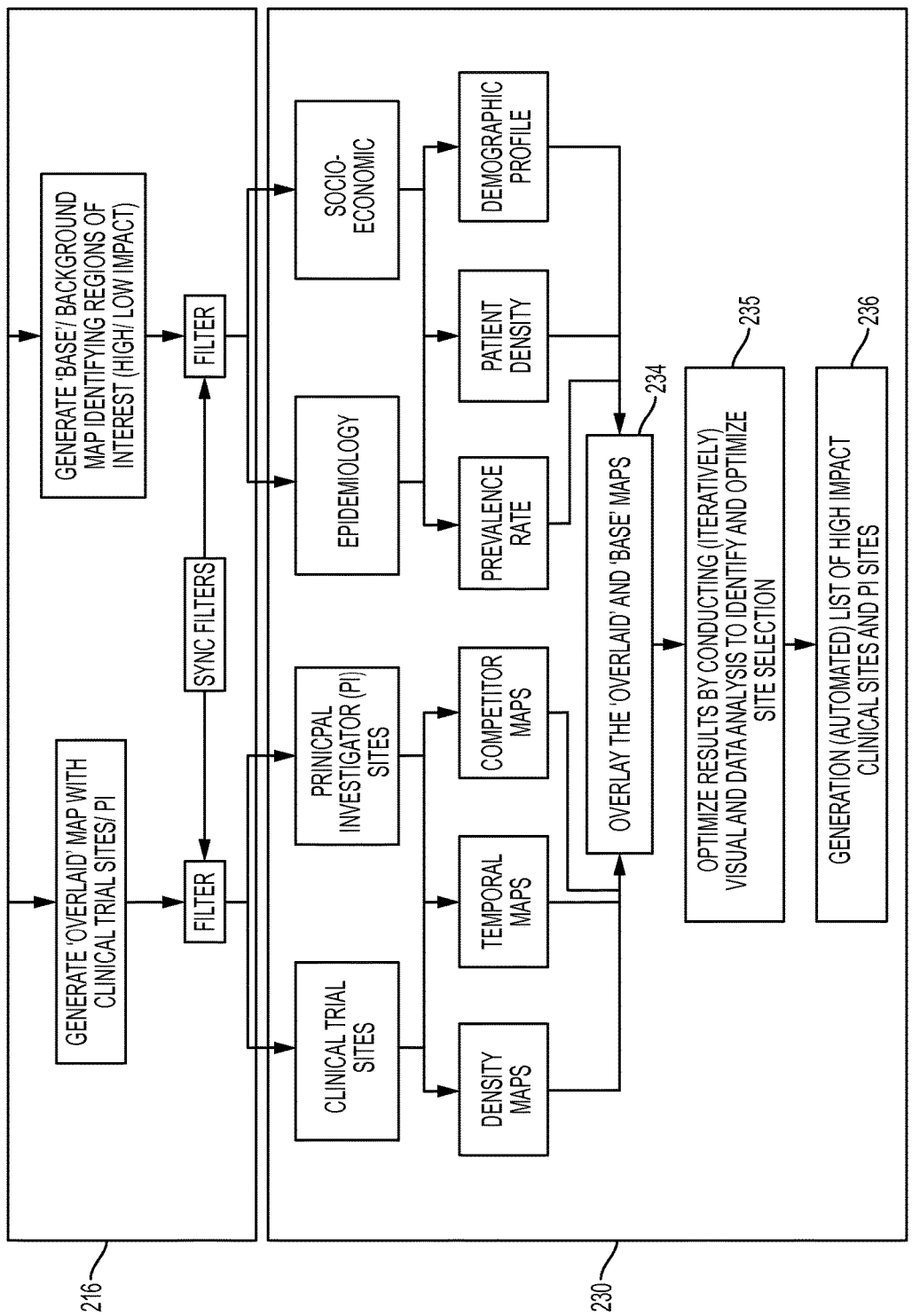

FIG. 2C illustrates a detailed description of step 230 of the algorithm of FIG. 2B, in accordance with embodiments of the present invention. In step 234, clinical trial sites are identified by:
1. Layering PI/clinical trial site information vs. patient density or prevalence rate information in
2. Layering PI/clinical trial sites information vs. PI or clinical trial site density information.
3. Analyzing competitor trial site information.
4. Executing a temporal analysis process.
5. Optimizing results associated with processes of step 218.
6. Generating a clinical trial site/PI list.

A process for layering PI/clinical trial site information vs. patient density or prevalence rate information comprises overlaying the clinical trial or PI site information over patient density or disease prevalence rate information to identify trial sites comprising higher changes of patient recruitment and completion of trial studies.

A process for layering PI/clinical trial sites information vs. PI or Clinical Trial Site density information comprises overlaying the clinical trial or PI site information over PI or clinical trial site density information to identify trial sites comprising higher PIs potentially conducting trials. The aforementioned process may be beneficial to the operational performance of clinical trial recruitment and performance.

A process for analyzing competitor sites information comprises overlaying the clinical trial or PI site information with respect to competitor information. The competitor information may include information with respect to past, current, or future clinical trials. The aforementioned process may be beneficial to understand a competitive landscape and identify trial sites.

A temporal analysis process may include overlaying the clinical trial or PI site information with respect to the epidemiology/socio economic data including a time component (year, month, day, etc.) for identifying a changing landscape in a temporal format. The aforementioned process may be beneficial to study and conduct analysis with respect to:
1. A pattern of clinical trial expansion or deployment of competing organizations.
2. Identifying new clinical trial sites freeing up for ongoing trials that are projected to end.
3. Changing landscape of disease prevalence and additional epidemiology and socioeconomic attributes.

In step 235, a process for optimizing results in executed. The process for optimizing results may include usage of different strategies and information sets to identify potentially good and bad sites to conduct clinical trials. The aforementioned process enables analysis and visualization that may be automated further to procure the latest data and generate potential target clinical trial sites and PIs.

In step 236, a process for generating a clinical trial site/PI list is executed. The process for generating a clinical trial site/PI list enables a process for generating a final list of potential client sites and PIs for targeting by clinical trial operational team. The final list may include site names, organization information, address, and related information.

Figure 3:
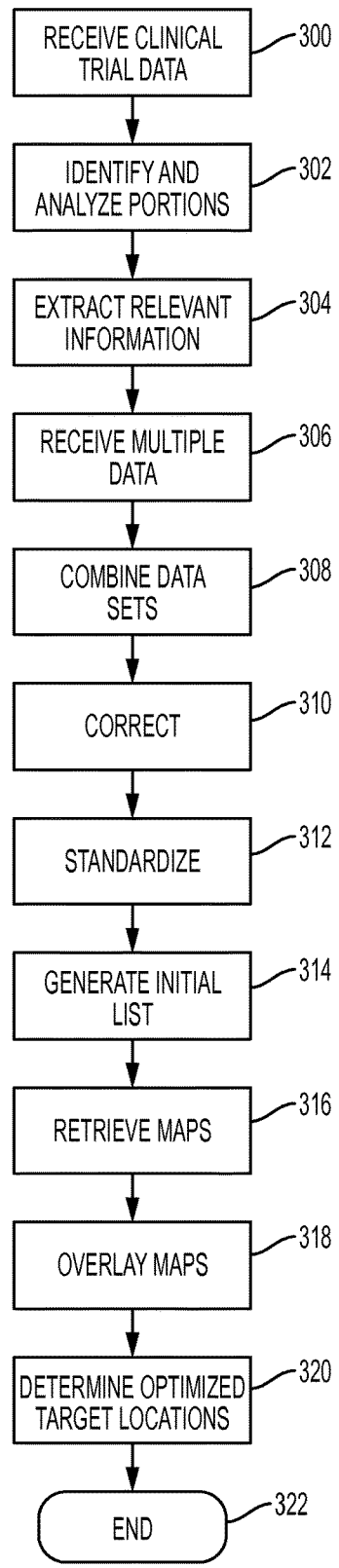
FIG. 3 illustrates an algorithm detailing a process flow enabled by the system of FIG. 1 for identifying clinical trial sites, in accordance with embodiments of the present invention.

FIG. 3 illustrates an algorithm detailing a process flow enabled by system 100 of FIG. 1 for identifying clinical trial sites, in accordance with embodiments of the present invention. Each of the steps in the algorithm of FIG. 3 may be enabled and executed in any order by a computer processor executing computer code. In step 300, clinical trial data (associated with a plurality of planned clinical trials, associated locations, and investigators) is received by a computing system from differing data sources. In step 302, portions of the clinical trial data identified and analyzed. In step 304, relevant information from the portions is extracted based on the analysis of step 302. In step 306, socioeconomic data, demographics data, and epidemiological data are received by the computing system. In step 308, differing sets of data of the clinical trial data, the socioeconomic data, the demographics data, and the epidemiological data are combined into a common format. In step 310, incorrect address data associated with the associated locations is corrected. In step 312, the clinical trial data, the socioeconomic data, the demographics data, and the epidemiological data are standardized. In step 314, an initial list is generated based on results of the standardization of step 312. The initial list includes associated principle investigators and clinical trial sites associated with the plurality of planned clinical trials overlaid on the clinical trial data, the socioeconomic data, the demographics data, and the epidemiological data. In step 316, background maps (identifying geographical regions comprising attributes of the plurality of planned clinical trials) and overlay maps (identifying target trial sites associated with the clinical trial data) are retrieved. In step 318, the background maps are overlaid with respect to the overlay maps. In step 320, a group of optimized target locations of the geographical regions and the trial sites is determined based on results of the overlaying of step 318. Additionally, the data associated with the principle investigators and the clinical trial sites may be overlaid with respect to a patient density of locations associated with the geographical regions and the trial sites and a modified group of optimized target locations of the geographical regions and the trial sites may be determined.

Figure 4:
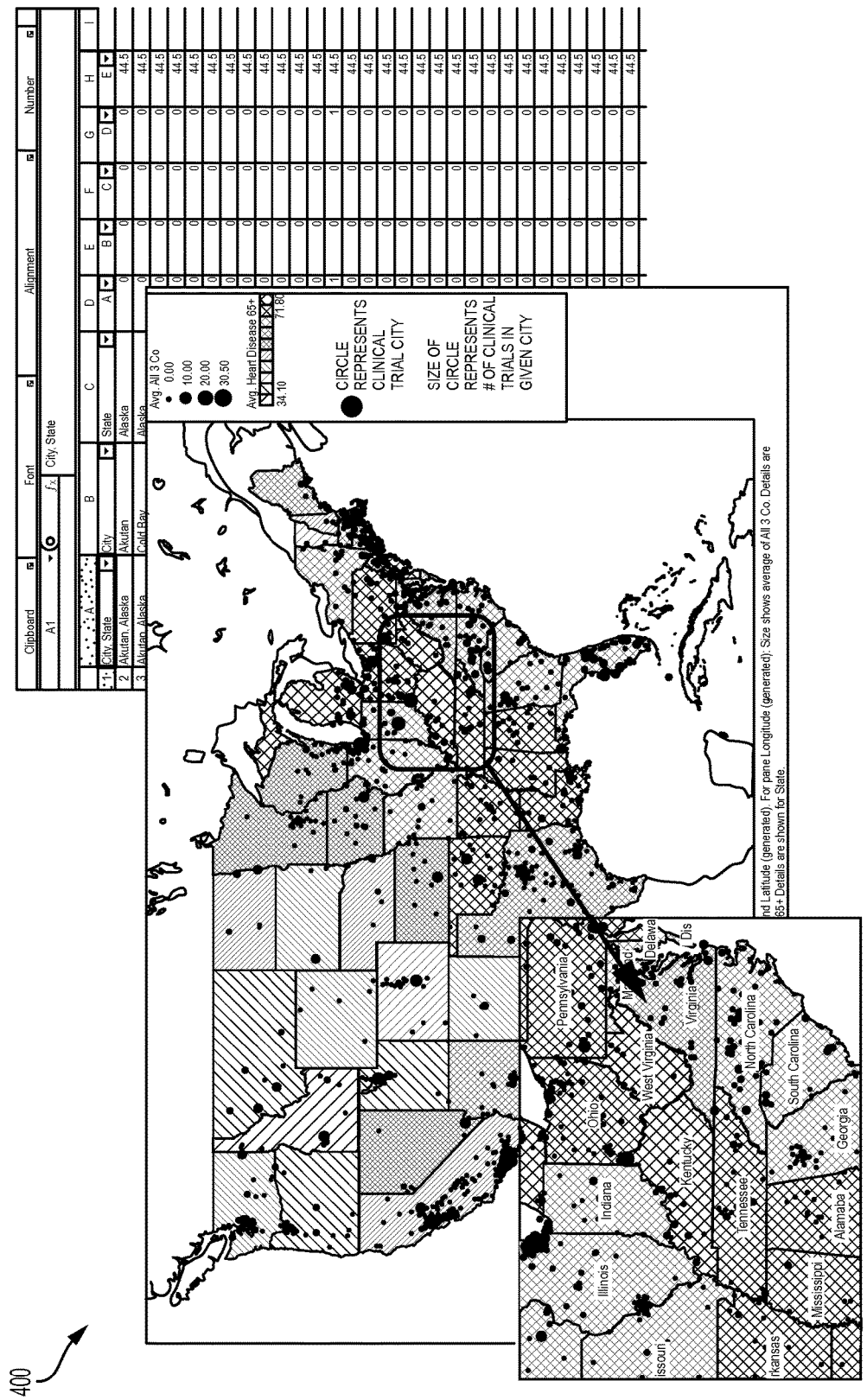
FIG. 4 illustrates a GUI for presenting visualization analysis of a proprotein convertase subtilisin/kexin type (9PCSK9) enzyme clinical trial sites, in accordance with embodiments of the present invention.

FIG. 4 illustrates a GUI 400 presenting a visualization analysis of a proprotein convertase subtilisin/kexin type (9PCSK9) enzyme clinical trial sites (overlaid map) overlaid with respect to epidemiology data associated with heart disease hospitalization rates in the United States (US) by state (base map), in accordance with embodiments of the present invention. The GUI 400 illustrates that it is evident that Kentucky and West Virginia have very high heart disease hospitalization rates, however very few clinical trials are being conducted in these locations thereby identifying target states that may be good candidates for conducting clinical trials such that an operational efficiency of recruitment may be higher. Additionally, GUI 400 identifies that there are less competing organizations conducting trials.

Figure 5:
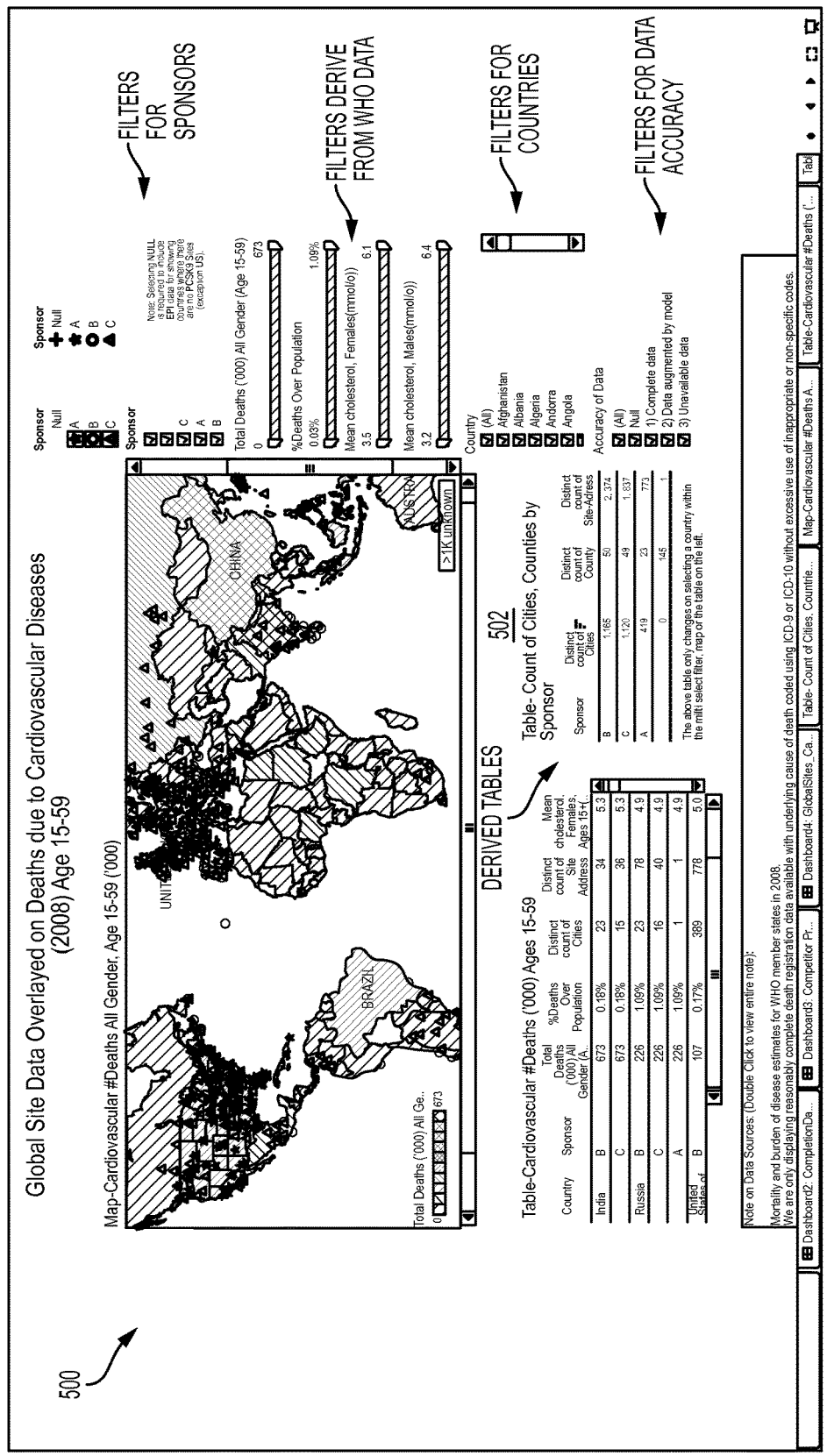
FIG. 5 illustrates a GUI for presenting a visualization analysis and data analysis conducted using software, in accordance with embodiments of the present invention.

FIG. 5 illustrates a GUI 500 for presenting a visualization analysis and data analysis conducted using Tableau BI software, in accordance with embodiments of the present invention. The GUI 500 illustrates an overlaid map of clinical trial site locations being conducted for a PCSK9 drug by three competing sponsor organizations being identified separately. The base map includes epidemiology information with respect to fatalities caused due to cardiovascular diseases at a country level. Multiple filters may be applied as follows:
1. For clinical trial sites such as a sponsor organization, country, etc.

2. With respect to epidemiology data such as a mean cholesterol level, gender, total fatalities and fatality rates, country, etc.

As the maps are overlaid, an analyst may perform scenario modeling to determine a best filter criteria that when applied will provide the most optimized results for targeting clinical trial sites. In addition to the maps, tables (i.e., derived tables 502) may be generated dynamically thereby providing important information and statistics that may enable analysts and strategists to identify the most promising regions to focus clinical trial operations. Visualization and data analysis tools/software may enable a process for automating and dynamically generating the aforementioned insights. Additionally, the visualization and data analysis tools/software may enable a process for setting optimized criteria associated with goals of the analyses. The GUI enables non-sophisticated data analysis to perform a strong data analysis process behind the scenes via this visually guided approach.

Figure 6:
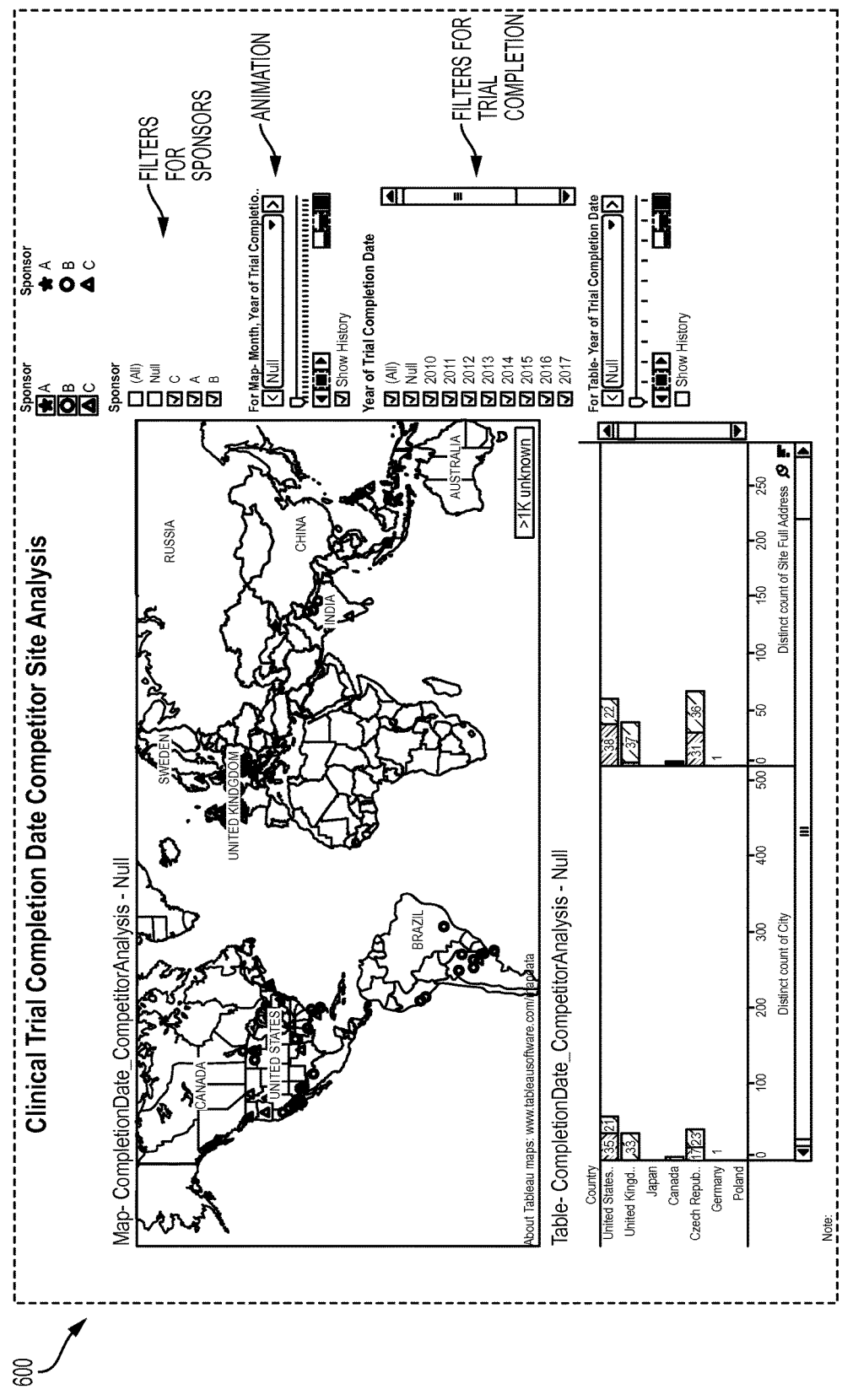
FIG. 6 illustrates a GUI for presenting temporal filters to provide insights with respect to different dimensions and criteria, in accordance with embodiments of the present invention.

FIG. 6 illustrates a GUI 600 for presenting temporal (time based) filters to provide insights with respect to different dimensions and criteria, in accordance with embodiments of the present invention. The temporal filters enable a temporal analysis that enables a sponsor organization to understand a changing landscape associated with clinical trials being conducted. The changing landscape allows a process for approaching more sites that are believed to free up from currently active trials. In addition to the clinical trial and epidemiology data, the time data also enables filtering a correct time frame for conducting analysis. Usage of the functionalities in the tool may help to identify clinical trial operationalizing strategies used by competing sponsor organizations. The aforementioned visual analysis, allows for identifying a number of clinical trials and site locations being conducted by sponsor organizations for specified time frames.

Figure 7:
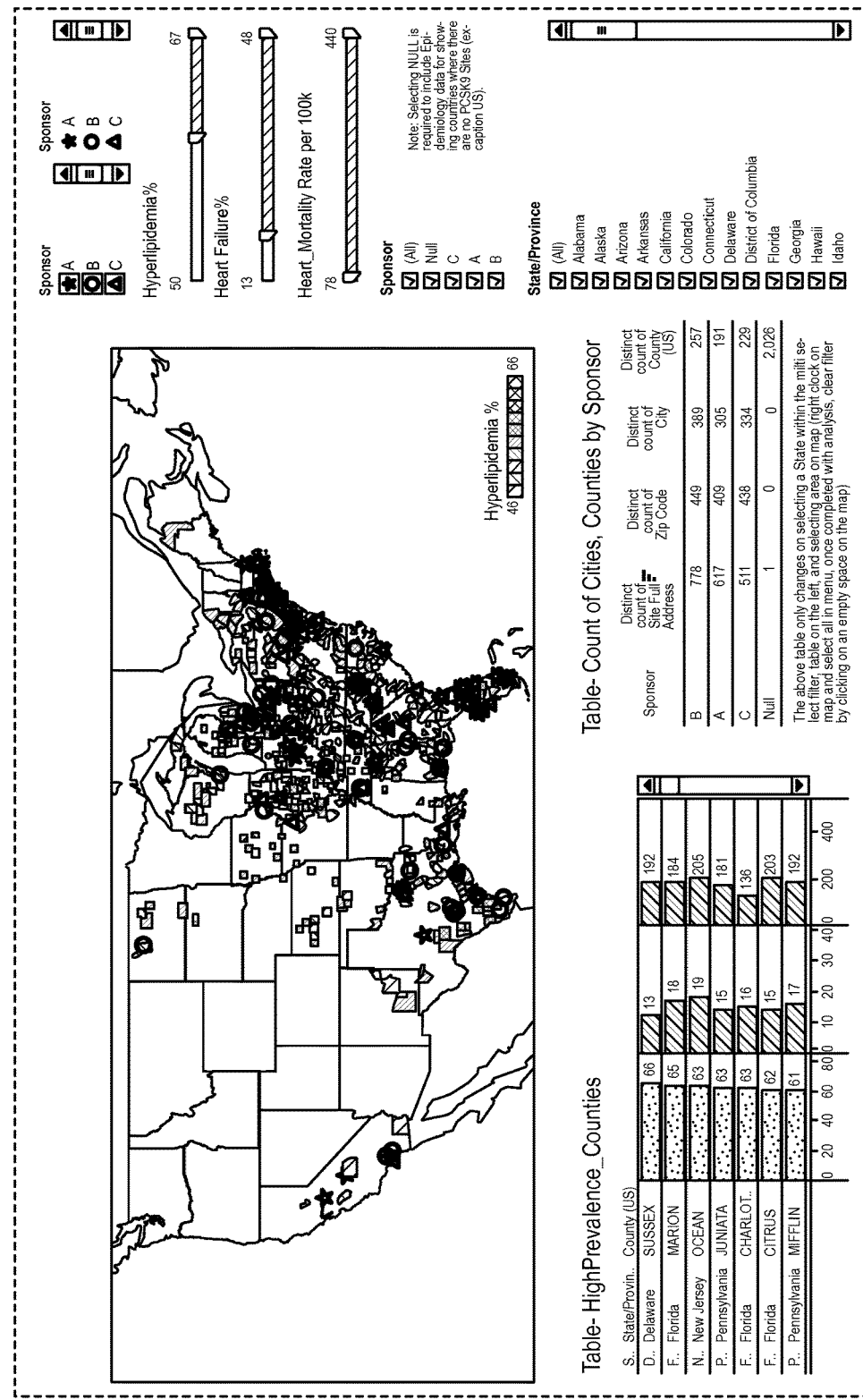
FIG. 7 illustrates a GUI for providing visual analysis performed at a differing granularity levels with respect to data and filters, in accordance with embodiments of the present invention.

FIG. 7 illustrates a GUI 700 for providing visual analysis performed at a differing granularity levels with respect to data and filters, in accordance with embodiments of the present invention. GUI 700 comprises an overlaid map including clinical trial site locations conducting PCSK9 drug trials by three competing sponsor organizations being identified separately. The base map comprises epidemiology information at a county level within the U.S., focusing on Hyperlipidemia prevalence rates. Multiple filters are applied as follows:
1. For clinical trial sites such as a sponsor organization, county, state, etc.
2. With respect to epidemiology data such as a hyperlipidemia prevalence rate (%), a heart failure rate, heart mortality rate, etc.

Upon overlaying the maps, an analyst may perform scenario modeling to determine a best filter criteria, that when applied, will provide the most optimized results for targeting clinical trial sites. In addition to the maps, tables (derived tables) may be generated dynamically for providing important information and statistics that may help analysts and strategists to identify the most promising regions to focus clinical trial operations. In this example (with respect to GUI 700), the tables identify a number of sites conducting clinical trials by sponsor organization, state, county, PI etc. as well as an epidemiology and demographic profile of those regions. The aforementioned insights may be very helpful for analysts and strategists to identify sweet spots that should be targeted for improved efficiency of trials. Receiving inputs from medical professionals, operational team, and clinical trial expert teams, allows the filters and data sets to be manipulated to achieve optimized clinical trial site and PI identification and list generation.

FIG. 8 illustrates a table 800 for providing formation and filters to drill down to identify most promising clinical trial sites and PIs, in accordance with embodiments of the present invention. Table 800 provides a list of cities and zip codes that fit the epidemiology profile that the clinical trial operational team is targeting (e.g., an average hyperlipidemia rate should be above 60%, an average heart failure should be above 15%, and an average heart mortality rate per 100 k should be greater than 130). Additionally, table 800 identifies which cities have already been covered by the sponsor organization and which ones have yet not been. The aforementioned type of analysis may be performed at a clinical trial site address level, PIs level, or at a health organization (hospital) level. The analysis enables automation of list generation such that when a more updated data set is received, results may be updated automatically thereby permitting a reduction in analysis time.

Figure 9:
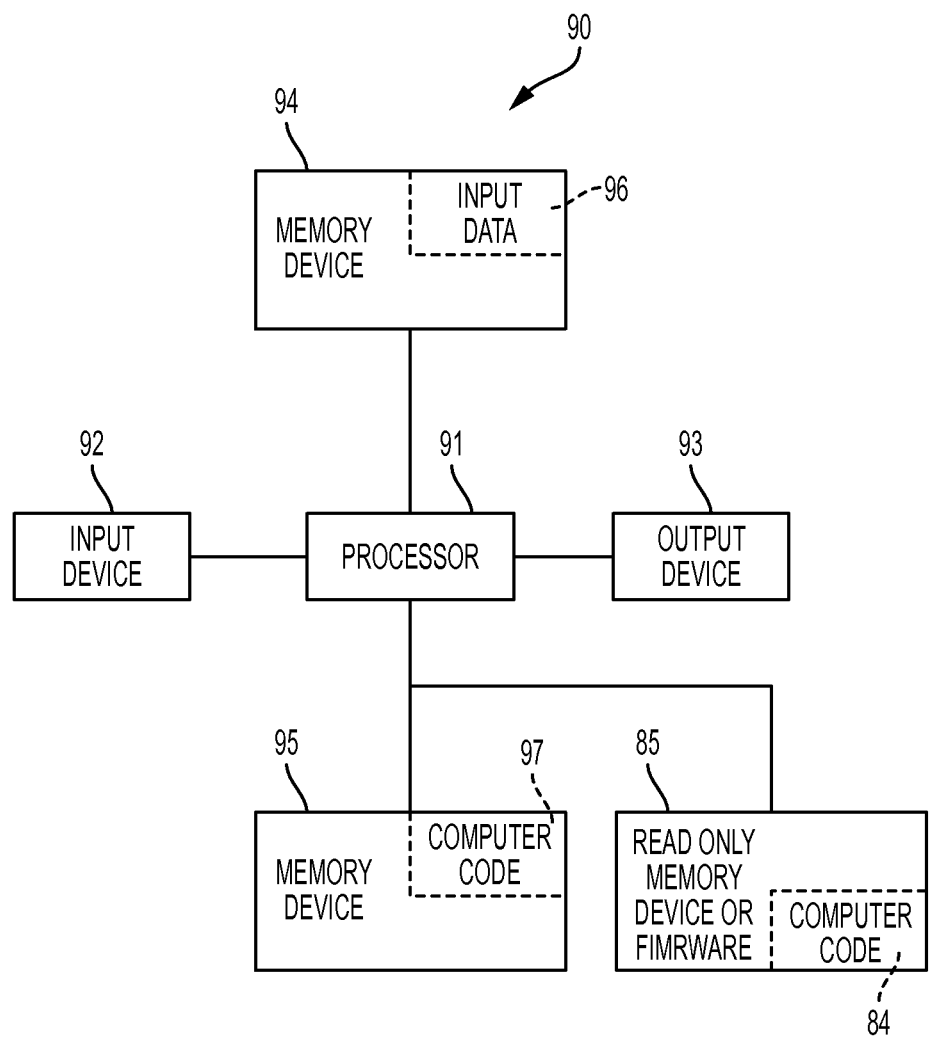
FIG. 9 illustrates a computer system for identifying clinical trial sites, in accordance with embodiments of the present invention.

FIG. 9 illustrates a computer system 90 (e.g., computing system 14 of FIG. 1) for identifying clinical trial sites, in accordance with embodiments of the present invention.

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive (SDD), a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing apparatus receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, device (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing device to produce a machine, such that the instructions, which execute via the processor of the computer or other programmable data processing device, create means for implementing the functions/acts specified in the flowchart and/or block diagram block or blocks. These computer readable program instructions may also be stored in a computer readable storage medium that can direct a computer, a programmable data processing device, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing device, or other device to cause a series of operational steps to be performed on the computer, other programmable device or other device to produce a computer implemented process, such that the instructions which execute on the computer, other programmable device, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The computer system 90 illustrated in FIG. 9 includes a processor 91, an input device 92 coupled to the processor 91, an output device 93 coupled to the processor 91, and memory devices 94 and 95 each coupled to the processor 91. The input device 92 may be, inter alia, a keyboard, a mouse, a camera, a touchscreen, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes algorithms (e.g., the algorithms of FIGS. 2 and 3) for identifying clinical trial sites. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices Such as read only memory device 96) may include the algorithms of FIGS. 2 and 3 and may be used as a computer usable medium (or a computer readable medium or a program storage device) having a computer readable program code embodied therein and/or having other data stored therein, wherein the computer readable program code includes the computer code 97. Generally, a computer program product (or, alternatively, an article of manufacture) of the computer system 90 may include the computer usable medium (or the program storage device).

In some embodiments, rather than being stored and accessed from a hard drive, optical disc or other writeable, rewriteable, or removable hardware memory device 95, stored computer program code 84 (e.g., including the algorithms of FIGS. 2 and 3) may be stored on a static, nonremovable, read-only storage medium such as a Read-Only Memory (ROM) device 85, or may be accessed by processor 103 directly from such a static, nonremovable, read-only medium 85. Similarly, in some embodiments, stored computer program code 84 may be stored as computer-readable firmware 85, or may be accessed by processor 103 directly from such firmware 85, rather than from a more dynamic or removable hardware data-storage device 95, such as a hard drive or optical disc.

Still yet, any of the components of the present invention could be created, integrated, hosted, maintained, deployed, managed, serviced, etc. by a service supplier who offers to identify clinical trial sites. Thus the present invention discloses a process for deploying, creating, integrating, hosting, maintaining, and/or integrating computing infrastructure, including integrating computer-readable code into the computer system 90, wherein the code in combination with the computer system 90 is capable of performing a method for identifying clinical trial sites. In another embodiment, the invention provides a business method that performs the process steps of the invention on a subscription, advertising, and/or fee basis. That is, a service supplier, such as a Solution Integrator, could offer to allow users to identify clinical trial sites. In this case, the service supplier can create, maintain, support, etc. a computer infrastructure that performs the process steps of the invention for one or more customers. In return, the service supplier can receive payment from the customer(s) under a subscription and/or fee agreement and/or the service supplier can receive payment from the sale of advertising content to one or more third parties.

While FIG. 9 shows the computer system 90 as a particular configuration of hardware and software, any configuration of hardware and software, as would be known to a person of ordinary skill in the art, may be utilized for the purposes stated supra in conjunction with the particular computer system 90 of FIG. 8. For example, the memory devices 94 and 95 may be portions of a single memory device rather than separate memory devices.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A clinical trial site geo location identification and visualization improvement method comprising:
   receiving, by a computer processor of a special purpose hardware system comprising special purpose hardware and computer instructions, clinical trial data associated with a plurality of planned clinical trials, associated locations, and investigators;
   identifying, by the computer processor, portions of the clinical trial data received from differing data sources;
   analyzing, by the computer processor, the portions;
   extracting, by the computer processor based on results of the analyzing, relevant information from the portions;
   receiving, by the computer processor, socioeconomic data, demographics data, and epidemiological data;
   combining into a common format, by the computer processor, different sets of data of the clinical trial data, the socioeconomic data, the demographics data, and the epidemiological data;
   correcting, by the computer processor executing a geo-spatial visualization tool, incorrect address data associated with the associated locations;
   executing, by the computer processor, a Web scraping process with respect to said socioeconomic data, demographics data, and epidemiological data;
   standardizing, by the computer processor, the clinical trial data, the socioeconomic data, the demographics data, and the epidemiological data;
   generating, by the computer processor based on results of the standardizing, an initial list comprising associated principle investigators and clinical trial sites associated with the plurality of planned clinical trials overlaid on the clinical trial data, the socioeconomic data, the demographics data, and the epidemiological data;
   retrieving, by the computer processor, background maps identifying geographical regions comprising attributes of the plurality of planned clinical trials;
   retrieving, by the computer processor, overlay maps identifying target trial sites associated with the clinical trial data;
   filtering, by said computer processor executing filtering circuits of said special purpose hardware system, attributes of said background maps and said overlay maps;
   enabling, by said computer processor, an advanced setting in said geo-spatial visualization tool thereby enabling atomization and synchronization of filters across said background maps and said overlay maps and visuals resulting in an increase of analytic performance, repeatability, and quality;
   overlaying, by the computer processor based on results of the filtering, the background maps with respect to the overlay maps;
   determining, by the computer processor based on results of the overlaying, a group of optimized target locations of the geographical regions and the trial sites; and
   conducting said planned clinical trials at said optimized target locations of the geographical regions and the trial sites.

2. The method of claim 1, further comprising:
   first overlaying, by the computer processor, the data associated with the principle investigators and the clinical trial sites with respect to a patient density of locations associated with the geographical regions and the trial sites; and
   determining, by the computer processor based on results of the first overlaying, a modified group of optimized target locations of the geographical regions and the trial sites.

3. The method of claim 1, further comprising:
   first overlaying, by the computer processor, the data associated with the principle investigators and the clinical trial sites with respect to a clinical trial site density of locations associated with the geographical regions and the trial sites; and
   determining, by the computer processor based on results of the first overlaying, a modified group of optimized target locations of the geographical regions and the trial sites.

4. The method of claim 3, wherein the data associated with the principle investigators and the clinical trial sites comprises competitor site data associated with competitor trial sites.

5. The method of claim 3, wherein the data associated with the principle investigators and the clinical trial sites comprises time related data.

6. A special purpose hardware system comprising special purpose hardware, computer instructions, and a computer processor coupled to a computer-readable memory unit, the memory unit comprising instructions that when executed by the computer processor implements a clinical trial site geo location identification and visualization improvement method comprising:
   receiving, by the computer processor, clinical trial data associated with a plurality of planned clinical trials, associated locations, and investigators;
   identifying, by the computer processor, portions of the clinical trial data received from differing data sources;
   analyzing, by the computer processor, the portions;

extracting, by the computer processor based on results of the analyzing, relevant information from the portions;

receiving, by the computer processor, socioeconomic data, demographics data, and epidemiological data;

combining into a common format, by the computer processor, different sets of data of the clinical trial data, the socioeconomic data, the demographics data, and the epidemiological data;

correcting, by the computer processor executing a geo-spatial visualization tool, incorrect address data associated with the associated locations;

executing, by the computer processor, a Web scraping process with respect to said socioeconomic data, demographics data, and epidemiological data;

standardizing, by the computer processor, the clinical trial data, the socioeconomic data, the demographics data, and the epidemiological data;

generating, by the computer processor based on results of the standardizing, an initial list comprising associated principle investigators and clinical trial sites associated with the plurality of planned clinical trials overlaid on the clinical trial data, the socioeconomic data, the demographics data, and the epidemiological data;

retrieving, by the computer processor, background maps identifying geographical regions comprising attributes of the plurality of planned clinical trials;

retrieving, by the computer processor, overlay maps identifying target trial sites associated with the clinical trial data;

filtering, by said computer processor executing filtering circuits of said special purpose hardware system, attributes of said background maps and said overlay maps;

enabling, by said computer processor, an advanced setting in said geo-spatial visualization tool thereby enabling atomization and synchronization of filters across said background maps and said overlay maps and visuals resulting in an increase of analytic performance, repeatability, and quality;

overlaying, by the computer processor based on results of the filtering, the background maps with respect to the overlay maps;

determining, by the computer processor based on results of the overlaying, a group of optimized target locations of the geographical regions and the trial sites; and conducting said planned clinical trials at said optimized target locations of the geographical regions and the trial sites.

7. The special purpose hardware system of claim 6, wherein the method further comprises:

first overlaying, by the computer processor, the data associated with the principle investigators and the clinical trial sites with respect to a patient density of locations associated with the geographical regions and the trial sites; and determining, by the computer processor based on results of the first overlaying, a modified group of optimized target locations of the geographical regions and the trial sites.

8. The special purpose hardware system of claim 6, wherein the method further comprises:

first overlaying, by the computer processor, the data associated with the principle investigators and the clinical trial sites with respect to a clinical trial site density of locations associated with the geographical regions and the trial sites; and determining, by the computer processor based on results of the first overlaying, a modified group of optimized target locations of the geographical regions and the trial sites.

9. The special purpose hardware system of claim 8, wherein the data associated with the principle investigators and the clinical trial sites comprises competitor site data associated with competitor trial sites.

10. The special purpose hardware system of claim 8, wherein the data associated with the principle investigators and the clinical trial sites comprises time related data.

11. A computer program product, comprising a computer readable hardware storage device storing a computer readable program code, the computer readable program code comprising an algorithm that when executed by a computer processor of a special purpose hardware system comprising special purpose hardware and computer instructions implements a clinical trial site geo location identification and visualization improvement method comprising:

receiving, by the computer processor, clinical trial data associated with a plurality of planned clinical trials, associated locations, and investigators;

identifying, by the computer processor, portions of the clinical trial data received from differing data sources;

analyzing, by the computer processor, the portions;

extracting, by the computer processor based on results of the analyzing, relevant information from the portions;

receiving, by the computer processor, socioeconomic data, demographics data, and epidemiological data;

combining into a common format, by the computer processor, different sets of data of the clinical trial data, the socioeconomic data, the demographics data, and the epidemiological data;

correcting, by the computer processor executing a geo-spatial visualization tool, incorrect address data associated with the associated locations;

executing, by the computer processor, a Web scraping process with respect to said socioeconomic data, demographics data, and epidemiological data;

standardizing, by the computer processor, the clinical trial data, the socioeconomic data, the demographics data, and the epidemiological data;

generating, by the computer processor based on results of the standardizing, an initial list comprising associated principle investigators and clinical trial sites associated with the plurality of planned clinical trials overlaid on the clinical trial data, the socioeconomic data, the demographics data, and the epidemiological data;

retrieving, by the computer processor, background maps identifying geographical regions comprising attributes of the plurality of planned clinical trials;

retrieving, by the computer processor, overlay maps identifying target trial sites associated with the clinical trial data;

filtering, by said computer processor executing filtering circuits of said special purpose hardware system, attributes of said background maps and said overlay maps;

enabling, by said computer processor, an advanced setting in said geo-spatial visualization tool thereby enabling atomization and synchronization of filters across said background maps and said overlay maps and visuals resulting in an increase of analytic performance, repeatability, and quality;

overlaying, by the computer processor based on results of the filtering, the background maps with respect to the overlay maps;

determining, by the computer processor based on results of the overlaying, a group of optimized target locations of the geographical regions and the trial sites; and conducting said planned clinical trials at said optimized target locations of the geographical regions and the trial sites.

12. The computer program product of claim 11, wherein the method further comprises:

first overlaying, by the computer processor, the data associated with the principle investigators and the clinical trial sites with respect to a patient density of locations associated with the geographical regions and the trial sites; and determining, by the computer processor based on results of the first overlaying, a modified group of optimized target locations of the geographical regions and the trial sites.

13. The computer program product of claim 11, wherein the method further comprises:

first overlaying, by the computer processor, the data associated with the principle investigators and the clinical trial sites with respect to a clinical trial site density of locations associated with the geographical regions and the trial sites; and determining, by the computer processor based on results of the first overlaying, a modified group of optimized target locations of the geographical regions and the trial sites.

14. The computer program product of claim 13, wherein the data associated with the principle investigators and the clinical trial sites comprises competitor site data associated with competitor trial sites.

15. The computer program product of claim 13, wherein the data associated with the principle investigators and the clinical trial sites comprises time related data.

16. A process for supporting computing infrastructure, the process comprising providing at least one support service for at least one of creating, integrating, hosting, maintaining, and deploying computer-readable code in a special purpose hardware system comprising special purpose hardware, computer instructions, and a computer processor, wherein the computer processor, in response to the providing, carries out instructions contained in the code causing the special purpose hardware system to perform a clinical trial site geo location identification and visualization improvement method comprising:

receiving, by the computer processor, clinical trial data associated with a plurality of planned clinical trials, associated locations, and investigators;

identifying, by the computer processor, portions of the clinical trial data received from differing data sources;

analyzing, by the computer processor, the portions;

extracting, by the computer processor based on results of the analyzing, relevant information from the portions;

receiving, by the computer processor, socioeconomic data, demographics data, and epidemiological data;

combining into a common format, by the computer processor, different sets of data of the clinical trial data, the socioeconomic data, the demographics data, and the epidemiological data;

correcting, by the computer processor executing a geo-spatial visualization tool, incorrect address data associated with the associated locations;

executing, by the computer processor, a Web scraping process with respect to said socioeconomic data, demographics data, and epidemiological data;

standardizing, by the computer processor, the clinical trial data, the socioeconomic data, the demographics data, and the epidemiological data;

generating, by the computer processor based on results of the standardizing, an initial list comprising associated principle investigators and clinical trial sites associated with the plurality of planned clinical trials overlaid on the clinical trial data, the socioeconomic data, the demographics data, and the epidemiological data;

retrieving, by the computer processor, background maps identifying geographical regions comprising attributes of the plurality of planned clinical trials;

retrieving, by the computer processor, overlay maps identifying target trial sites associated with the clinical trial data;

filtering, by said computer processor executing filtering circuits of said special purpose hardware system, attributes of said background maps and said overlay maps;

enabling, by said computer processor, an advanced setting in said geo-spatial visualization tool thereby enabling atomization and synchronization of filters across said background maps and said overlay maps and visuals resulting in an increase of analytic performance, repeatability, and quality;

overlaying, by the computer processor based on results of the filtering, the background maps with respect to the overlay maps;

determining, by the computer processor based on results of the overlaying, a group of optimized target locations of the geographical regions and the trial sites; and conducting said planned clinical trials at said optimized target locations of the geographical regions and the trial sites.

17. The process of claim 16, wherein the method further comprises:

first overlaying, by the computer processor, the data associated with the principle investigators and the clinical trial sites with respect to a patient density of locations associated with the geographical regions and the trial sites; and determining, by the computer processor based on results of the first overlaying, a modified group of optimized target locations of the geographical regions and the trial sites.

18. The process of claim 16, wherein the method further comprises:

first overlaying, by the computer processor, the data associated with the principle investigators and the clinical trial sites with respect to a clinical trial site density of locations associated with the geographical regions and the trial sites; and determining, by the computer processor based on results of the first overlaying, a modified group of optimized target locations of the geographical regions and the trial sites.

19. The process of claim 18, wherein the data associated with the principle investigators and the clinical trial sites comprises competitor site data associated with competitor trial sites.

20. The process of claim 18, wherein the data associated with the principle investigators and the clinical trial sites comprises time related data.

21. A clinical trial site geo location identification and visualization improvement method comprising:

receiving, by a computer processor of a special purpose hardware system comprising special purpose hardware and computer instructions, clinical trial data associated with a plurality of planned clinical trials, associated locations, and investigators;

identifying, by the computer processor, portions of the clinical trial data received from differing data sources;

analyzing, by the computer processor, the portions;

extracting, by the computer processor based on results of the analyzing, relevant information from the portions;

receiving, by the computer processor, socioeconomic data, demographics data, and epidemiological data;

executing, by the computer processor, a Web scraping process with respect to said socioeconomic data, demographics data, epidemiological data, and publically available data of the portions;

combining into a common format, by the computer processor based on results of the executing, different sets of data of the clinical trial data, the socioeconomic data, the demographics data, and the epidemiological data;

correcting, by the computer processor executing a geo-spatial visualization tool, incorrect address data associated with the associated locations;

standardizing, by the computer processor, the clinical trial data, the socioeconomic data, the demographics data, and the epidemiological data;

generating, by the computer processor based on results of the standardizing, an initial list comprising associated principle investigators and clinical trial sites associated with the plurality of planned clinical trials overlaid on the clinical trial data, the socioeconomic data, the demographics data, and the epidemiological data;

retrieving, by the computer processor, background maps identifying geographical regions comprising attributes of the plurality of planned clinical trials;

retrieving, by the computer processor, overlay maps identifying target trial sites associated with the clinical trial data;

filtering, by said computer processor executing filtering circuits of said special purpose hardware system, attributes of said background maps and said overlay maps;

enabling, by said computer processor, an advanced setting in said geo-spatial visualization tool thereby enabling atomization and synchronization of filters across said background maps and said overlay maps and visuals resulting in an increase of analytic performance, repeatability, and quality;

overlaying, by the computer processor based on results of the filtering, the background maps with respect to the overlay maps;

determining, by the computer processor based on results of the overlaying, a group of optimized target locations of the geographical regions and the trial sites; and conducting said planned clinical trials at said optimized target locations of the geographical regions and the trial sites.

* * * * *